(12) United States Patent
Neumann

(10) Patent No.: US 12,087,443 B2
(45) Date of Patent: Sep. 10, 2024

(54) SYSTEM AND METHOD FOR TRANSMITTING A SEVERITY VECTOR

(71) Applicant: KPN INNOVATIONS, LLC., Lakewood, CO (US)

(72) Inventor: Kenneth Neumann, Lakewood, CO (US)

(73) Assignee: KPN INNOVATIONS LLC, Lakewood, CO (US)

(*) Notice: Subject to any disclaimer, the term of this patent is extended or adjusted under 35 U.S.C. 154(b) by 12 days.

(21) Appl. No.: 17/062,779

(22) Filed: Oct. 5, 2020

(65) Prior Publication Data
US 2022/0108799 A1 Apr. 7, 2022

(51) Int. Cl.
G16H 50/20 (2018.01)
G06N 20/00 (2019.01)

(52) U.S. Cl.
CPC ............ *G16H 50/20* (2018.01); *G06N 20/00* (2019.01)

(58) Field of Classification Search
CPC ........ G16H 50/20; G16H 50/70; G06F 19/30; G06F 19/32; G06F 19/324; G06F 19/34; G06Q 50/22; G06Q 50/24; G06N 20/00; G06N 3/045; G06N 5/01; G06N 3/08; Y02A 90/10
See application file for complete search history.

(56) References Cited

U.S. PATENT DOCUMENTS

| | | | |
|---|---|---|---|
| 5,778,893 A * | 7/1998 | Potter | G16H 50/20 128/898 |
| 7,953,613 B2 | 5/2011 | Gizewski | |
| 8,766,803 B2 | 7/2014 | Bousamra et al. | |
| 10,314,547 B2 | 6/2019 | Miller et al. | |
| 10,360,343 B2 | 7/2019 | Prakash | |
| 10,368,810 B2 | 8/2019 | Quinn et al. | |
| 2003/0036683 A1 | 2/2003 | Kehr | |
| 2004/0221855 A1 * | 11/2004 | Ashton | G06F 19/345 128/898 |
| 2011/0119212 A1 * | 5/2011 | De Bruin | A61B 5/0476 706/12 |
| 2013/0218588 A1 | 8/2013 | Kehr et al. | |
| 2018/0113982 A1 | 4/2018 | Asthana et al. | |

(Continued)

OTHER PUBLICATIONS

Graham et al., "Identifying clusters of health symptoms in deployed military personnel and their relationship with probable PTSD", (Year: 2019).*

(Continued)

*Primary Examiner* — Eliza A Lam
(74) *Attorney, Agent, or Firm* — Caldwell Intellectual Property Law

(57) ABSTRACT

A system for presenting a severity vector includes a computing device configured to obtain a user status from a remote device, identify a user affliction as a function of a user status, generate an effect enumeration as a function of the affliction, wherein generating includes receiving an affliction training set correlating at least a first element of an affliction state and at least a first affliction result and generating an effect enumeration as a function of the affliction training set using an affliction machine-learning process, wherein the affliction machine-learning process is trained using the affliction training set, calculate a severity vector, and transmit the severity score on the remote device.

20 Claims, 6 Drawing Sheets

(56) References Cited

U.S. PATENT DOCUMENTS

| | | | |
|---|---|---|---|
| 2019/0019575 A1* | 1/2019 | Apte | G16H 10/60 |
| 2019/0355473 A1* | 11/2019 | Schobel | G16H 50/30 |
| 2020/0185100 A1 | 6/2020 | Francois | |
| 2020/0211717 A1* | 7/2020 | Albert | A61B 5/7275 |
| 2020/0253562 A1* | 8/2020 | Newberry | A61B 5/4845 |
| 2020/0357526 A1* | 11/2020 | Odiz | G16H 10/40 |
| 2022/0369977 A1* | 11/2022 | Wang | A61B 5/16 |

OTHER PUBLICATIONS https://www.mdpi.com/2079-4991/9/6/813.
https://www.himss.org/resources/wearable-technology-applications-healthcare-literature-review.
http://www.selectsmart.com/fitnesstracker/.

* cited by examiner

SYSTEM AND METHOD FOR TRANSMITTING A SEVERITY VECTOR

FIELD OF THE INVENTION

The present invention generally relates to the field of network communication and processing. In particular, the present invention is directed to a system and method for presenting a severity vector.

BACKGROUND

Current user afflictions develop at unknown rates with unique symptoms. This leads to inefficient affliction amelioration as the affliction is ever growing and changing.

SUMMARY OF THE DISCLOSURE

In an aspect, a system for transmitting a severity vector includes a computing device configured to obtain, from a remote device, a user status, identify a user affliction as a function of a user status, wherein the user status is generated as a function of an affliction classifier, the affliction classifier generated using a user machine-learning process, generate an effect enumeration as a function of the affliction, wherein generating includes receiving an affliction training set correlating at least a first element of an affliction state and at least a first affliction result and generating an effect enumeration as a function of the affliction training set using an affliction machine-learning process, wherein the affliction machine-learning process is trained using the affliction training set, calculate a severity vector, wherein calculating includes receiving a severity training set correlating an effect enumeration to an affliction status and calculating the severity vector as a function of the severity training set using a severity machine-learning process, wherein the severity machine-learning process is configured using the severity training set, and transmit the severity score on the remote device.

In an another aspect, a method for transmitting a severity vector includes obtaining, by a computing device, a user status from a remote device, identifying, by a computing device, a user affliction as a function of a user status, wherein the user status is generated as a function of an affliction classifier, the affliction classifier generated using a user machine-learning process, generating, by a computing device, an effect enumeration as a function of the affliction, wherein generating includes receiving an affliction training set correlating at least a first element of an affliction state and at least a first affliction result and generating an effect enumeration as a function of the affliction training set using an affliction machine-learning process, wherein the affliction machine-learning process is trained using the affliction training set, calculating, by a computing device, a severity vector, wherein calculating includes receiving a severity training set correlating an effect enumeration to an affliction status and calculating the severity vector as a function of the severity training set using a severity machine-learning process, wherein the severity machine-learning process is configured using the severity training set, and transmitting, by a computing device, the severity score on the remote device.

These and other aspects and features of non-limiting embodiments of the present invention will become apparent to those skilled in the art upon review of the following description of specific non-limiting embodiments of the invention in conjunction with the accompanying drawings.

BRIEF DESCRIPTION OF THE DRAWINGS

For the purpose of illustrating the invention, the drawings show aspects of one or more embodiments of the invention. However, it should be understood that the present invention is not limited to the precise arrangements and instrumentalities shown in the drawings, wherein.

The drawings are not necessarily to scale and may be illustrated by phantom lines, diagrammatic representations and fragmentary views. In certain instances, details that are not necessary for an understanding of the embodiments or that render other details difficult to perceive may have been omitted.

DETAILED DESCRIPTION

At a high level, aspects of the present disclosure are directed to systems and methods for transmitting a severity vector. In an embodiment, this system transmits a severity vector as a function of a user affliction. In an embodiment, this system determines a proneness a user will experience subsequent symptoms associated with an affliction. Embodiments may be used to predict user affliction symptoms and complications. This may be so, at least in part, because system obtains a biological extraction from the user and generates, via a machine-learning process, the severity vector that specifies the proneness of developing subsequent symptoms. Exemplary embodiments illustrating aspects of the present disclosure are described below in the context of several specific examples.

Figure 1:
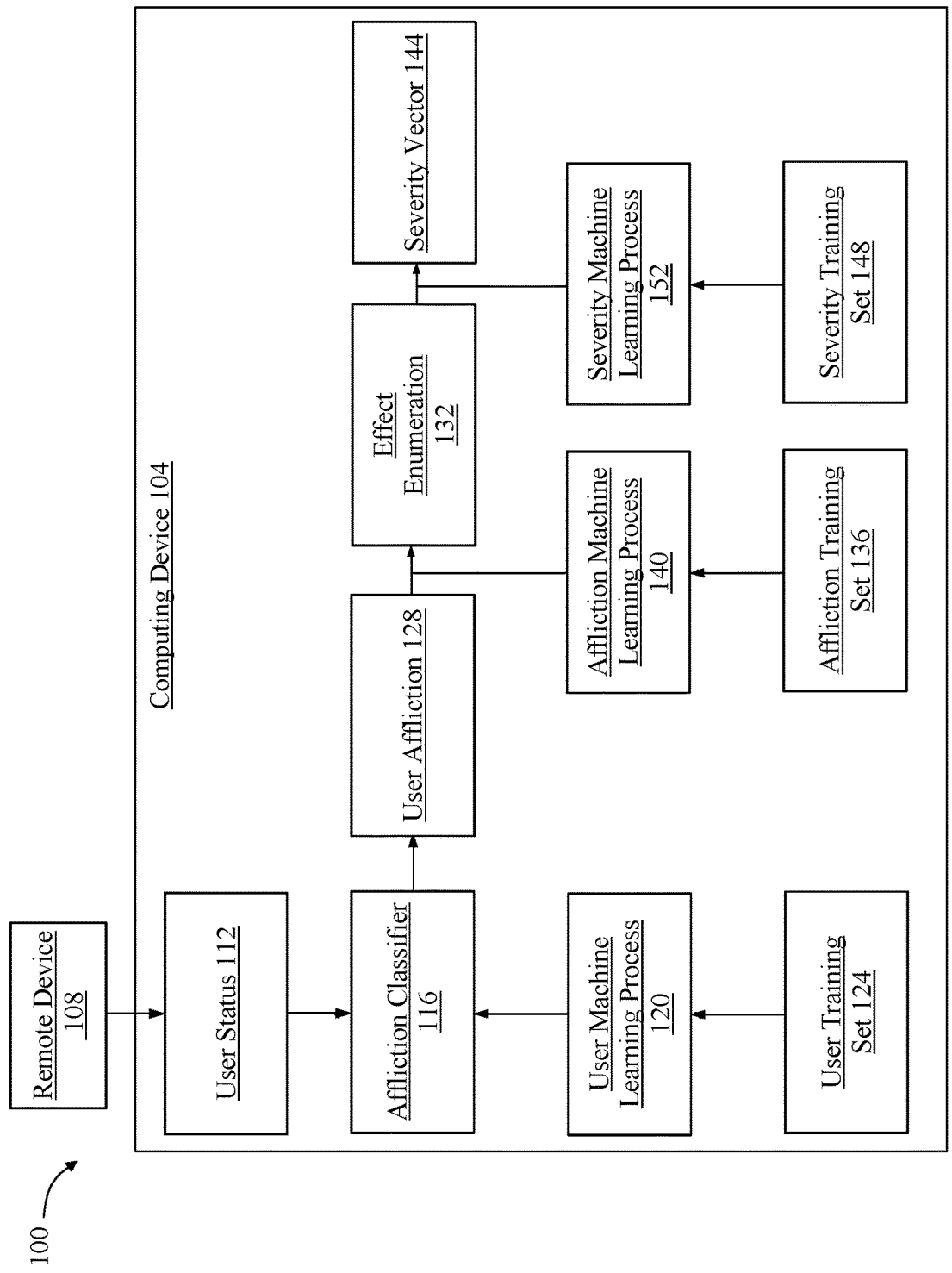
FIG. 1 is a block diagram illustrating an exemplary embodiment of a system for transmitting a severity vector.

Referring now to FIG. 1, an exemplary embodiment of a system 100 for representing an arranged list of provider aliment possibilities is illustrated. System 100 includes a computing device 104. Computing device 104 may include any computing device as described in this disclosure, including without limitation a microcontroller, microprocessor, digital signal processor (DSP) and/or system on a chip (SoC) as described in this disclosure. Computing device 104 may include, be included in, and/or communicate with a mobile device such as a mobile telephone or smartphone. Computing device 104 may include a single computing device operating independently, or may include two or more computing device operating in concert, in parallel, sequentially or the like; two or more computing devices may be included together in a single computing device or in two or more computing devices. Computing device 104 may interface or communicate with one or more additional devices as described below in further detail via a network interface device. Network interface device may be utilized for connecting computing device 104 to one or more of a variety of networks, and one or more devices. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any possibilities thereof. A network may employ a wired and/or a wireless mode of communication. In general, any network topology may be used. Information (e.g., data, software etc.) may be communicated to and/or from a computer and/or a computing device. Computing device 104 may include but is not limited to, for example, a computing device or cluster of computing devices in a first location and a second computing device or cluster of computing devices in a second location. Computing device 104 may include one or more computing devices dedicated to data storage, security, distribution of traffic for load balancing, and the like. Computing device 104 may distribute one or more computing tasks as described below across a plurality of computing devices of computing device, which may operate in parallel, in series, redundantly, or in any other manner used for distribution of tasks or memory between computing devices. Computing device 104 may be implemented using a "shared nothing" architecture in which data is cached at the worker, in an embodiment, this may enable scalability of system 100 and/or computing device.

With continued reference to FIG. 1. computing device 104 may be designed and/or configured to perform any method, method step, or sequence of method steps in any embodiment described in this disclosure, in any order and with any degree of repetition. For instance, computing device 104 may be configured to perform a single step or sequence repeatedly until a desired or commanded outcome is achieved; repetition of a step or a sequence of steps may be performed iteratively and/or recursively using outputs of previous repetitions as inputs to subsequent repetitions, aggregating inputs and/or outputs of repetitions to produce an aggregate result, reduction or decrement of one or more variables such as global variables, and/or division of a larger processing task into a set of iteratively addressed smaller processing tasks. Computing device 104 may perform any step or sequence of steps as described in this disclosure in parallel, such as simultaneously and/or substantially simultaneously performing a step two or more times using two or more parallel threads, processor cores, or the like; division of tasks between parallel threads and/or processes may be performed according to any protocol suitable for division of tasks between iterations. Persons skilled in the art, upon reviewing the entirety of this disclosure, will be aware of various ways in which steps, sequences of steps, processing tasks, and/or data may be subdivided, shared, or otherwise dealt with using iteration, recursion, and/or parallel processing.

Still referring to FIG. 1, computing device 104 is configured to obtain, from a remote device 108, a user status 112. As used in this disclosure "remote device" is a device, which may include any device suitable for use as computing device 104, in communication with computing device 104. Remote device 108 may include any display as described herein. Remote device 108 may include an additional computing device, such as a mobile device, laptop, desktop, computer, and the like. Remote device 108 may transmit and/or receive one or more inputs from computing device 104 utilizing any network methodology as described herein. In an embodiment, a user or any acquaintance of the user may enter on his/her mobile device a user status 112, which may transmit to computing device 104 utilizing any network methodology as described herein. As used in this disclosure a "user status" is an element of data including one or more affliction vectors relating to the user, wherein an affliction vector is further comprised of one or more qualitative elements that may indicate the current health status of a user. For example, an affliction vector may include, without limitation, a physician input, a self-report, a questionnaire, a survey, familial input, acquaintance input, or biological extraction. For example, a user's physician may input to remote device 108 that a user has an affliction vector of high blood pressure and a high LDL value, which will be transmitted to computing device 104 as the current user status. A "biological extraction" as used in this disclosure includes at least an element of user biological data. As used in this disclosure, "biological data" is data indicative of a person's biological state; biological state may be evaluated with regard to one or more measures of health of a person's body, one or more systems within a person's body such as a circulatory system, a digestive system, a nervous system, or the like, one or more organs within a person's body, and/or any other subdivision of a person's body useful for diagnostic or prognostic purposes. For instance, and without limitation, a particular set of biomarkers, test results, and/or biochemical information may be recognized in a given medical field as useful for identifying various disease conditions or prognoses within a relevant field. As a non-limiting example, and without limitation, biological data describing red blood cells, such as red blood cell count, hemoglobin levels, hematocrit, mean corpuscular volume, mean corpuscular hemoglobin, and/or mean corpuscular hemoglobin concentration may be recognized as useful for identifying various conditions such as dehydration, high testosterone, nutrient deficiencies, kidney dysfunction, chronic inflammation, anemia, and/or blood loss. Biological extraction data may alternatively or additionally include any data used as a biological extraction as described in U.S. Nonprovisional application Ser. No. 16/502,835, filed on Jul. 3, 2019, and entitled "METHODS AND SYSTEMS FOR ACHIEVING VIBRANT CONSTITUTION BASED ON USER INPUTS," the entirety of which is incorporated herein by reference.

Still referring to FIG. 1, computing device 104 may be configured to identify an affliction classifier 116 as a function of user status 112. As used in this disclosure "affliction classifier" which as used in this disclosure is a machine-learning model as defined below, such as a mathematical model, neural net, or program generated by a machine-learning algorithm known as a "classification algorithm," as described in further detail below, that sorts inputs into categories or bins of data, outputting the categories or bins of data and/or labels associated therewith. Additionally or alternatively affliction classifier 116 may be configured to output at least a datum that labels or otherwise identifies a set of data that are clustered together. For example, affliction classifier 116 may include, without limitation, clustering of similar data such as high blood pressure and heart disease as they both relate to the circulatory system. For example, affliction classifier 116 may include, without limitation, clustering of data associated with both physical and psychological afflictions, such as depression and decreased quantities of dopamine in the user. Affliction classifier 116 may comprise qualitative elements. As used in this disclosure a "qualitative element" is a biological extraction, user demographic, medical lineage, medical history, and the like thereof. For example, a qualitative element may include a medical lineage of breast cancer or ovarian cancer, which may be used as a qualitative element for affliction classifier 116. Affliction classifier 116 may output mensurable values relating the qualitative element, wherein a measurable value associated with the qualitative element is generated. As used in this disclosure "mensurable values" are one or more values in a decimal, binary, octal, hexadecimal, or duodecimal number system. For example, a mensurable output may consist of a value of 5 for a qualitative element of no medical history associated with lung cancer, wherein a value of 100 may be outputted due to a qualitative element of smoking as a medical history element.

Still referring to FIG. 1, computing device 104 may identify affliction classifier 116 using a user machine-learning process 120. As used in this disclosure "user machine-learning process" is a supervised, unsupervised, or reinforcement machine-learning process that computing system 104 may or may not use in the determination of the affliction classifier. User machine-learning process 120 may include, without limitation, any machine-learning process such as simple linear regression, multiple linear regression, polynomial regression, support vector regression, ridge regression, lasso regression, elasticnet regression, decision tree regression, random forest regression, logistic regression, logistic classification, K-nearest neighbours, support vector machines, kernel support vector machines, naïve bayes, decision tree classification, random forest classification, K-means clustering, hierarchical clustering, dimensionality reduction, principal component analysis, linear discriminant analysis, kernel principal component analysis, Q-learning, State Action Reward State Action (SARSA), Deep-Q network, markov decision processes, or Deep Deterministic Policy Gradient (DDPG). User machine-learning process 120 may be configured as a function of a user training set 124. A "user training set", as used in this disclosure relates a user element to an affliction. For example, and without limitation, user training set 136 may relate a high glucose concentration to diabetes. For example, and without limitation, user training set 136 may relate a fever and encephalitis with West Nile virus. As used in this disclosure, a "user element" is a qualitative and/or mensurable element relating to the user. For example, and without limitation, a user element may include a concentration of glucose in the user's circulatory system. For example, and without limitation, a user element may include medical history of previously contracting COVID-19.

Still referring to FIG. 1, computing device 104 is configured to identify a user affliction 128 as a function of affliction classifier 116. As used in this disclosure, a "user affliction" is an ailment and/or list or collection of ailments; ailments may include, without limitation, physical, spiritual, and/or psychological ailments correlating to any resulting impact on the user. For example, a physical affliction may include, without limitation, COVID-19, CRE, Ebola, Enterovirus D68, Influenza, Hantavirus, Hepatitis A, Hepatitis A, HIV/AIDS, Diabetes (Type I or Type II), Multiple Sclerosis, Chron's Disease, Colitis, Lupus, Rheumatoid Arthritis, Allergies, Asthma, Relapsing Polychondritis, Scleroderma, Liver Disease, Heart Disease, Cancer, and the like thereof. For example, a spiritual affliction may include, without limitation, religious conflicts, chakra blockages, existential crisis, or the like thereof. For example a psychological affliction may include, without limitation, Alzheimer's, Parkinson's, alcohol or substance abuse disorder, anxiety disorder, ADD, ADHD, bipolar disorder, depression, eating disorder, obsessive-compulsive disorder, opioid use disorder, PTSD, schizophrenia, depersonalization disorder, dissociative amnesia and/or fatigue, anorexia, bulimia, sleep disorders, wake disorders, paraphilic disorders, sexual disorders, child mental disorders, personality disorders, gender dysphoria, depression, and the like thereof. Persons skilled in the art, upon reviewing the entirety of this disclosure, will be aware of various alternative or additional user afflictions that may be used consistently with this disclosure. Additionally or alternatively, computing device 104 may identify user affliction 128 as a function of the mensurable output generated by the affliction classifier. For example, and without limitation, affliction classifier 116 may output a mensurable value of 5 corresponding to the user affliction of influenza, while affliction classifier may also output a mensurable value of 100 corresponding to the user affliction of COVID-19. User affliction 128 may then determine the user affliction is COVID-19 as opposed to influenza.

Still referring to FIG. 1, computing device 104 is configured to generate an effect enumeration 132 as a function of user status 112. As used in this disclosure "effect enumeration" is a probability vector associated with developing subsequent symptoms associated with user affliction 128. For example, and without limitation, computing device 104 may generate an effect enumeration of ARDS, myocarditis, delayed cognitive function, and pneumonia for the affliction of COVID-19. Computing device generates effect enumeration 112 by receiving an affliction training set 136. As used in this disclosure "affliction training set" is at least a first element of an affliction state and at least a first affliction result, wherein an element of an affliction state may include, without limitation, current signs, symptoms, and impacts an affliction has on the user and correlates the elements of the affliction states to affliction result possibilities. For example, and without limitation, a sign of coughing as an element of an affliction state input may correlate to an affliction result of upper respiratory infection. Computing device 104 then generates effect enumeration 132 as a function of affliction training set 136 using an affliction machine-learning process 140. As used in this disclosure "affliction machine-learning process" is a supervised, unsupervised, or reinforcement machine-learning process that computing system 104 may or may not use in the determination of the enumeration outcome. Affliction machine-learning process 140 may include, without limitation, any machine-learning process such as simple linear regression, multiple linear regression, polynomial regression, support vector regression, ridge regression, lasso regression, elasticnet regression, decision tree regression, random forest regression, logistic regression, logistic classification, K-nearest neighbours, support vector machines, kernel support vector machines, naïve bayes, decision tree classification, random forest classification, K-means clustering, hierarchical clustering, dimensionality reduction, principal component analysis, linear discriminant analysis, kernel principal component analysis, Q-learning, State Action Reward State Action (SARSA), Deep-Q network, markov decision processes, or Deep Deterministic Policy Gradient (DDPG).

Still referring to FIG. 1, effect enumeration 132 may include a plurality of enumeration elements associated with the affliction. As used in this disclosure "enumeration elements" is a biological impact, symptom, or effect an affliction has on a user. For example, enumeration elements may include, without limitation, acne, arthritis, coughing, sneezing, congestion, headache, swelling, vertigo, itching, rashes, increase and/or decrease blood pressure, internal bleeding, clots, nausea, stomach pain, loss of appetite, colored urine, colored stools, jaundice, trouble breathing, and the like thereof. Additionally or alternatively, enumeration elements may correspond to an affliction result. For example, and without limitation, COVID-19 may have enumeration elements including, but not limited to, fatigue, cough, shortness of breath, headache, joint pain, myocarditis, heart failure, pneumonia, scarring of alveoli, strokes, seizures, Guillain-Barre syndrome, Parkinson's, Alzheimer's, blood clots, posttraumatic stress syndrome, chronic fatigue syndrome, and the like thereof. Each enumeration element may correspond to an affliction result. As used in this disclosure an "affliction result" is a potential symptom and/or potential impact an affliction has on a user. For example, an enumeration element of coughing, may result in an affliction result of an upper respiratory element, while an enumeration element of sneezing may result in an affliction result of influenza. A further example may include an enumeration element corresponding to a plurality of affliction results, such as respiratory distress may result in a plurality of affliction results such as, but not limited to, pneumonia, coughing, shortness of breath, decreased $O_2$ saturation, and the like thereof.

With continued reference to FIG. 1, computing device 104 calculates a severity vector 144 as a function of effect enumeration 132. As used in this disclosure "severity vector" is a value representing the proneness for a user affliction to progress into subsequent symptoms and/or impacts. For example, and without limitation, a severity vector may indicate a proneness for developing respiratory distress for influenza due to the predisposition of asthma. Severity vector may be comprised of a measurable index relating to the proneness of developing affliction symptoms. As used in this disclosure "measurable index" is a decimal, binary, octal, hexadecimal, or duodecimal number system that relates the proneness of developing a system to a numerical value. For example, and without limitation, a user affliction may be COVID-19 and may have a medical history of ischemic heart disease, warranting a value of 100 for a severity vector in the proneness of developing myocarditis as a result of COVID-19. For example, and without limitation, a user affliction may be influenza and may have a medical history of ischemic heart disease, warranting a value of 5 for a severity vector in the proneness of developing myocarditis because of influenza. Severity vector values may indicate one or more severity values that correspond to a plurality of effect enumerations. For example, a severity vector may be calculated for West Nile Virus, wherein a severity value may be generated for comorbidities, permanent damage, death, period of incapacitation, bed rest, cognitive dysfunction, and the like thereof.

Still referring to FIG. 1, computing device 104 may calculate severity vector 144 by receiving a severity training set 148. As used in this disclosure "severity training set" relates effect enumeration 132 to an affliction status. In an embodiment, and without limitation, an effect enumeration for influenza may be cough, fever, respiratory distress, decreased $O_2$ saturation level, cognitive dysfunction, death, and the like thereof, which may be related to the current affliction status of a user affliction. As used in this disclosure "affliction status" relates to the current state of an affliction. For example, with reference to above, a user may have an affliction relating to influenza and may be experiencing a cough, wherein the affliction status is early and has not elevated to respiratory distress, decreased $O_2$ saturation level, cognitive dysfunction, death, and the like thereof. For example, and without limitation, a symptom of a fever may be an early state of COVID-19, while pneumonia may be a later state of COVID-19. Computing device 104 calculates severity vector 144 as a function of severity training set 148 using a severity machine-learning process 152. As used in this disclosure "severity machine-learning process" is a supervised, unsupervised, or reinforcement machine-learning process that computing system 104 may or may not use in the determination of severity vector 144. Severity machine-learning process 152 may include, without limitation, any machine-learning process such as simple linear regression, multiple linear regression, polynomial regression, support vector regression, ridge regression, lasso regression, elasticnet regression, decision tree regression, random forest regression, logistic regression, logistic classification, K-nearest neighbours, support vector machines, kernel support vector machines, naïve bayes, decision tree classification, random forest classification, K-means clustering, hierarchical clustering, dimensionality reduction, principal component analysis, linear discriminant analysis, kernel principal component analysis, Q-learning, State Action Reward State Action (SARSA), Deep-Q network, markov decision processes, or Deep Deterministic Policy Gradient (DDPG).

Still referring to FIG. 1, computing device 104 is configured to transmit severity vector 144 on remote device 108. Remote device 108 may include any display as described above. Remote device 108 may include an additional computing device, such as a mobile device, laptop, desktop, computer, and the like. Remote device 108 may transmit and/or receive one or more inputs from computing device 104 utilizing any network methodology as described herein. In an embodiment, remote device 132 may display severity vector 144 of a plurality of severity vectors and allow the user to navigate through all severity vectors to determine the most likely affliction progression. As used in this disclosure an "affliction progression" is a future symptom, impact, or effect that user affliction 128 has on the user. For example, an affliction progression of developing a fever may be presented to a user, wherein the user has an affliction of rhinovirus.

Figure 2:
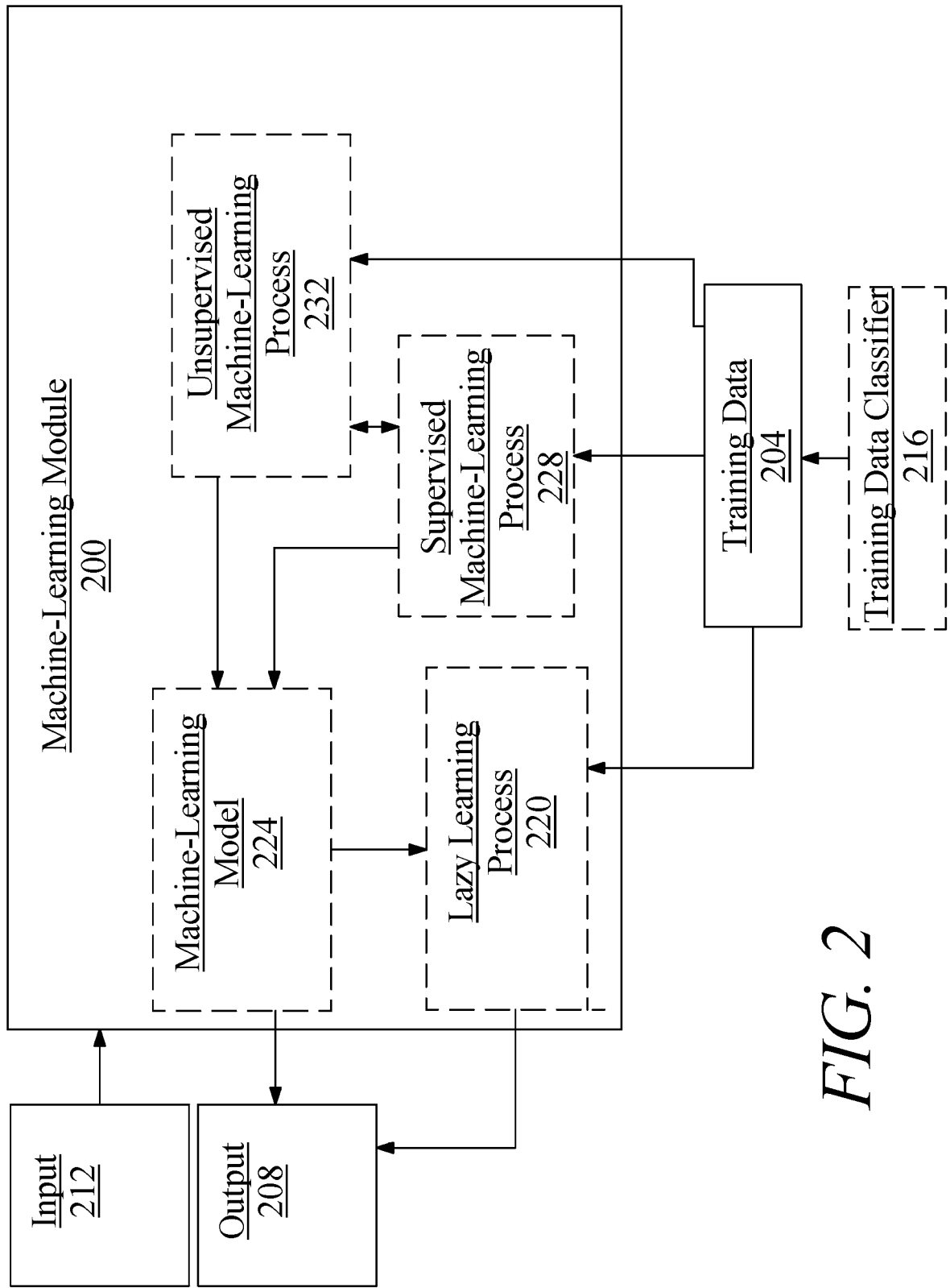
FIG. 2 is a block diagram of an exemplary embodiment of a machine-learning module.

Referring now to FIG. 2, an exemplary embodiment of a machine-learning module 200 that may perform one or more machine-learning processes as described in this disclosure is illustrated. Machine-learning module may perform determinations, classification, and/or analysis steps, methods, processes, or the like as described in this disclosure using machine-learning processes. A "machine-learning process," as used in this disclosure, is a process that automatedly uses training data 204 to generate an algorithm that will be performed by a computing device/module to produce outputs 208 given data provided as inputs 212; this is in contrast to a non-machine-learning software program where the commands to be executed are determined in advance by a user and written in a programming language.

Still referring to FIG. 2, "training data," as used herein, is data containing correlations that a machine-learning process may use to model relationships between two or more categories of data elements. For instance, and without limitation, training data 204 may include user training set, affliction training set, severity training set, among a plurality of other data entries, each entry representing a set of data elements that were recorded, received, and/or generated together; data elements may be correlated by shared existence in a given data entry, by proximity in a given data entry, or the like. Multiple data entries in training data 204 may evince one or more trends in correlations between categories of data elements; for instance, and without limitation, a higher value of a first data element belonging to a first category of data element may tend to correlate to a higher value of a second data element belonging to a second category of data element, indicating a possible proportional or other mathematical relationship linking values belonging to the two categories. Multiple categories of data elements may be related in training data 204 according to various correlations; correlations may indicate causative and/or predictive links between categories of data elements, which may be modeled as relationships such as mathematical relationships by machine-learning processes as described in further detail below. Training data 204 may be formatted and/or organized by categories of data elements, for instance by associating data elements with one or more descriptors corresponding to categories of data elements. As a non-limiting example, training data 204 may include data entered in standardized forms by persons or processes, such that entry of a given data element in a given field in a form may be mapped to one or more descriptors of categories. Elements in training data 204 may be linked to descriptors of categories by tags, tokens, or other data elements; for instance, and without limitation, training data 204 may be provided in fixed-length formats, formats linking positions of data to categories such as comma-separated value (CSV) formats and/or self-describing formats such as extensible markup language (XML), JavaScript Object Notation (JSON), or the like, enabling processes or devices to detect categories of data.

Alternatively or additionally, and continuing to refer to FIG. 2, training data 204 may include one or more elements that are not categorized; that is, training data 204 may not be formatted or contain descriptors for some elements of data. Machine-learning algorithms and/or other processes may sort training data 204 according to one or more categorizations using, for instance, natural language processing algorithms, tokenization, detection of correlated values in raw data and the like; categories may be generated using correlation and/or other processing algorithms. As a non-limiting example, in a corpus of text, phrases making up a number "n" of compound words, such as nouns updated by other nouns, may be identified according to a statistically significant prevalence of n-grams containing such words in a particular order; such an n-gram may be categorized as an element of language such as a "word" to be tracked similarly to single words, generating a new category as a result of statistical analysis. Similarly, in a data entry including some textual data, a person's name may be identified by reference to a list, dictionary, or other compendium of terms, permitting ad-hoc categorization by machine-learning algorithms, and/or automated association of data in the data entry with descriptors or into a given format. The ability to categorize data entries automatedly may enable the same training data 204 to be made applicable for two or more distinct machine-learning algorithms as described in further detail below. Training data 204 used by machine-learning module 200 may correlate any input data as described in this disclosure to any output data as described in this disclosure. As a non-limiting illustrative example, a severity training set may be an input, wherein severity machine-learning model may output the severity vector.

Further referring to FIG. 2, training data may be filtered, sorted, and/or selected using one or more supervised and/or unsupervised machine-learning processes and/or models as described in further detail below; such models may include without limitation a training data classifier 216. Training data classifier 216 may include a "classifier," which as used in this disclosure is a machine-learning model as defined below, such as a mathematical model, neural net, or program generated by a machine-learning algorithm known as a "classification algorithm," as described in further detail below, that sorts inputs into categories or bins of data, outputting the categories or bins of data and/or labels associated therewith. A classifier may be configured to output at least a datum that labels or otherwise identifies a set of data that are clustered together, found to be close under a distance metric as described below, or the like. Machine-learning module 200 may generate a classifier using a classification algorithm, defined as a process whereby a computing device and/or any module and/or component operating thereon derives a classifier from training data 204. Classification may be performed using, without limitation, linear classifiers such as without limitation logistic regression and/or naive Bayes classifiers, nearest neighbor classifiers such as k-nearest neighbors classifiers, support vector machines, least squares support vector machines, fisher's linear discriminant, quadratic classifiers, decision trees, boosted trees, random forest classifiers, learning vector quantization, and/or neural network-based classifiers. As a non-limiting example, training data classifier 216 may classify elements of training data to specific severity vectors where a severity vector type may be classified based on the location of the user condition in the body.

Still referring to FIG. 2, machine-learning module 200 may be configured to perform a lazy-learning process 220 and/or protocol, which may alternatively be referred to as a "lazy loading" or "call-when-needed" process and/or protocol, may be a process whereby machine-learning is conducted upon receipt of an input to be converted to an output, by combining the input and training set to derive the algorithm to be used to produce the output on demand. For instance, an initial set of simulations may be performed to cover an initial heuristic and/or "first guess" at an output and/or relationship. As a non-limiting example, an initial heuristic may include a ranking of associations between inputs and elements of training data 204. Heuristic may include selecting some number of highest-ranking associations and/or training data 204 elements. Lazy learning may implement any suitable lazy learning algorithm, including without limitation a K-nearest neighbors algorithm, a lazy naïve Bayes algorithm, or the like; persons skilled in the art, upon reviewing the entirety of this disclosure, will be aware of various lazy-learning algorithms that may be applied to generate outputs as described in this disclosure, including without limitation lazy learning applications of machine-learning algorithms as described in further detail below.

Alternatively or additionally, and with continued reference to FIG. 2, machine-learning processes as described in this disclosure may be used to generate machine-learning models 224. A "machine-learning model," as used in this disclosure, is a mathematical and/or algorithmic representation of a relationship between inputs and outputs, as generated using any machine-learning process including without limitation any process as described above, and stored in memory; an input is submitted to a machine-learning model 224 once created, which generates an output based on the relationship that was derived. For instance, and without limitation, a linear regression model, generated using a linear regression algorithm, may compute a linear combination of input data using coefficients derived during machine-learning processes to calculate an output datum. As a further non-limiting example, a machine-learning model 224 may be generated by creating an artificial neural network, such as a convolutional neural network comprising an input layer of nodes, one or more intermediate layers, and an output layer of nodes. Connections between nodes may be created via the process of "training" the network, in which elements from a training data 204 set are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning.

Still referring to FIG. 2, machine-learning algorithms may include at least a supervised machine-learning process 228. At least a supervised machine-learning process 228, as defined herein, include algorithms that receive a training set relating a number of inputs to a number of outputs, and seek to find one or more mathematical relations relating inputs to outputs, where each of the one or more mathematical relations is optimal according to some criterion specified to the algorithm using some scoring function. For instance, a supervised learning algorithm may include severity training set as described above as inputs, severity vector as outputs, and a scoring function representing a desired form of relationship to be detected between inputs and outputs; scoring function may, for instance, seek to maximize the probability that a given input and/or combination of elements inputs is associated with a given output to minimize the probability that a given input is not associated with a given output. Scoring function may be expressed as a risk function representing an "expected loss" of an algorithm relating inputs to outputs, where loss is computed as an error function representing a degree to which a prediction generated by the relation is incorrect when compared to a given input-output pair provided in training data 204. Persons skilled in the art, upon reviewing the entirety of this disclosure, will be aware of various possible variations of at least a supervised machine-learning process 228 that may be used to determine relation between inputs and outputs. Supervised machine-learning processes may include classification algorithms as defined above.

Further referring to FIG. 2, machine-learning processes may include at least an unsupervised machine-learning processes 232. An unsupervised machine-learning process, as used herein, is a process that derives inferences in datasets without regard to labels; as a result, an unsupervised machine-learning process may be free to discover any structure, relationship, and/or correlation provided in the data. Unsupervised processes may not require a response variable; unsupervised processes may be used to find interesting patterns and/or inferences between variables, to determine a degree of correlation between two or more variables, or the like.

Still referring to FIG. 2, machine-learning module 200 may be designed and configured to create a machine-learning model 224 using techniques for development of linear regression models. Linear regression models may include ordinary least squares regression, which aims to minimize the square of the difference between predicted outcomes and actual outcomes according to an appropriate norm for measuring such a difference (e.g. a vector-space distance norm); coefficients of the resulting linear equation may be updated to improve minimization. Linear regression models may include ridge regression methods, where the function to be minimized includes the least-squares function plus term multiplying the square of each coefficient by a scalar amount to penalize large coefficients. Linear regression models may include least absolute shrinkage and selection operator (LASSO) models, in which ridge regression is combined with multiplying the least-squares term by a factor of 1 divided by double the number of samples. Linear regression models may include a multi-task lasso model wherein the norm applied in the least-squares term of the lasso model is the Frobenius norm amounting to the square root of the sum of squares of all terms. Linear regression models may include the elastic net model, a multi-task elastic net model, a least angle regression model, a LARS lasso model, an orthogonal matching pursuit model, a Bayesian regression model, a logistic regression model, a stochastic gradient descent model, a perceptron model, a passive aggressive algorithm, a robustness regression model, a Huber regression model, or any other suitable model that may occur to persons skilled in the art upon reviewing the entirety of this disclosure. Linear regression models may be generalized in an embodiment to polynomial regression models, whereby a polynomial equation (e.g. a quadratic, cubic or higher-order equation) providing a best predicted output/actual output fit is sought; similar methods to those described above may be applied to minimize error functions, as will be apparent to persons skilled in the art upon reviewing the entirety of this disclosure.

Continuing to refer to FIG. 2, machine-learning algorithms may include, without limitation, linear discriminant analysis. Machine-learning algorithm may include quadratic discriminate analysis. Machine-learning algorithms may include kernel ridge regression. Machine-learning algorithms may include support vector machines, including without limitation support vector classification-based regression processes. Machine-learning algorithms may include stochastic gradient descent algorithms, including classification and regression algorithms based on stochastic gradient descent. Machine-learning algorithms may include nearest neighbors algorithms. Machine-learning algorithms may include Gaussian processes such as Gaussian Process Regression. Machine-learning algorithms may include cross-decomposition algorithms, including partial least squares and/or canonical correlation analysis. Machine-learning algorithms may include naïve Bayes methods. Machine-learning algorithms may include algorithms based on decision trees, such as decision tree classification or regression algorithms. Machine-learning algorithms may include ensemble methods such as bagging meta-estimator, forest of randomized tress, AdaBoost, gradient tree boosting, and/or voting classifier methods. Machine-learning algorithms may include neural net algorithms, including convolutional neural net processes.

Still referring to FIG. 2, models may be generated using alternative or additional artificial intelligence methods, including without limitation by creating an artificial neural network, such as a convolutional neural network comprising an input layer of nodes, one or more intermediate layers, and an output layer of nodes. Connections between nodes may be created via the process of "training" the network, in which elements from a training data 204 set are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning. This network may be trained using training data 204.

Figure 3:
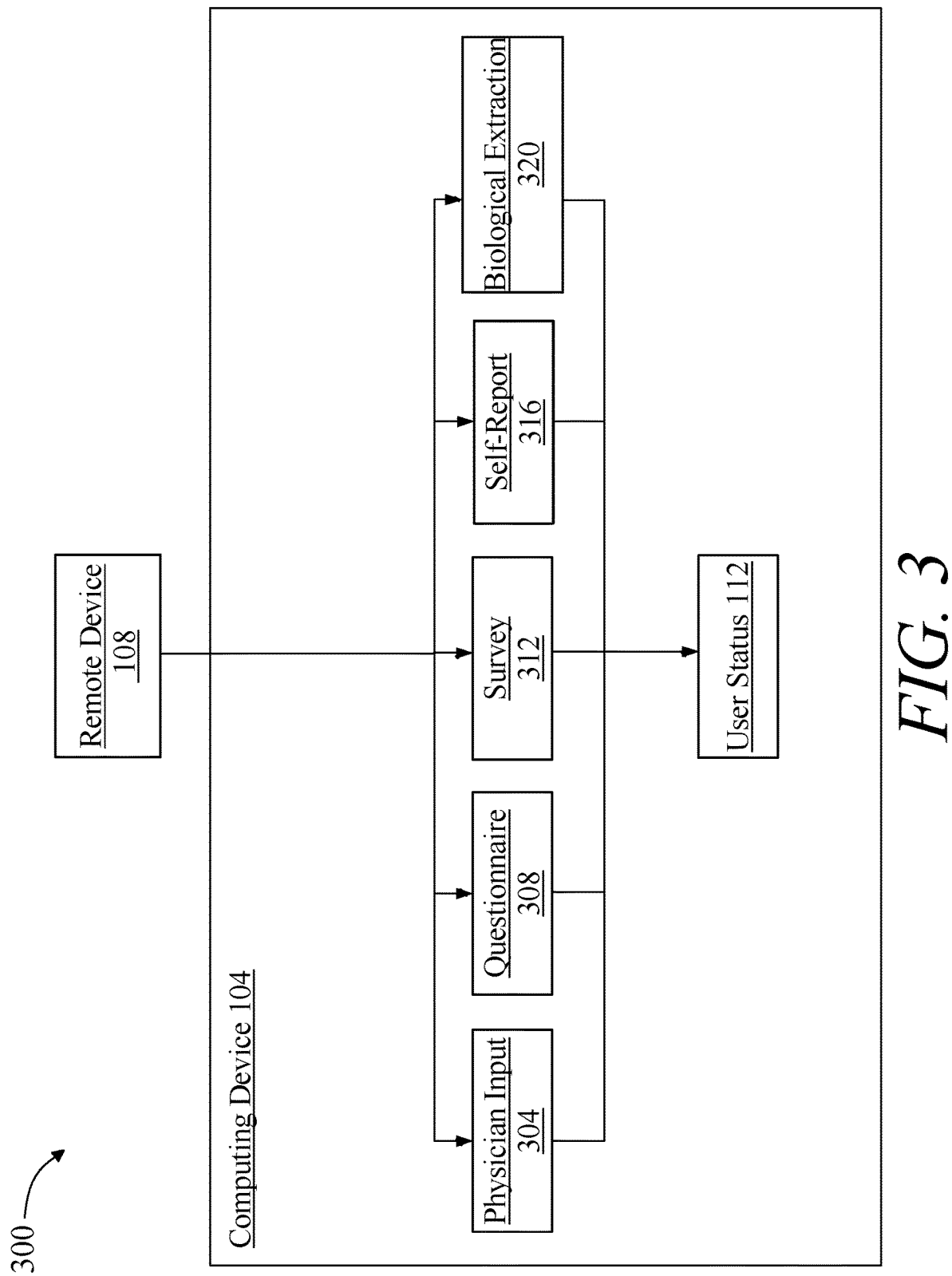
FIG. 3 is a block diagram of an exemplary embodiment of remote device outputs according to an embodiment of the invention.

Now referring to FIG. 3, an exemplary embodiment of 300 of a remote device input according to an embodiment of the invention is illustrated. Computing device 104 may receive qualitive outputs from remote device 108 and provide the qualitative outputs as inputs to user status 112. Qualitative elements may be any non-numerical descriptor relating the user to a class, category, or cluster that may identify a user status. Remote device 108 outputs may be comprised of a physician input 304. As used in this disclosure "physician input" is input provided from a medical professional such as a doctor, nurse, nurse practitioner, functional medicine practitioner, pharmacist, physician assistant, and/or any professional with a career in medicine, nutrition, genetics, fitness, life sciences, insurance, and/or any other applicable industry. For example, and without limitation, physician 304 input may be comprised of entering discolored stool as an input to user status 112. Remote device 108 outputs may further be comprised of a questionnaire 308. As used in this disclosure a "questionnaire" is a written set of questions of a plurality of written questions that may indicate one or more characteristics, qualities, or traits associated with user status 112. For example, and without limitation, questionnaire 308 may include providing a user with a written form in which the user has to answer about any symptoms, signs, or affliction impacts they may be experiencing. Remote device 108 outputs may further be comprised of a survey 312. As used in this disclosure a "survey" is a written or verbal set of questions, wherein the process of collecting, aggregating, and analyzing the responses provides a qualitative element to user status 112. For example, and without limitation, survey 312 may consist of a verbal set of questions that relate one or more signs, symptoms, or impacts associated with a user affliction. Remote device 108 outputs may further be comprised of a self-report, by a user family friends, or the like thereof. As used in this disclosure "self-report" is a self-generated, written, or recorded descriptor associated with user status 112. For example, and without limitation self-report may include a family member, friend, acquaintance, or the like thereof entering a user status relating to the signs, symptoms, and/or impacts associated with a user. Remote device 108 outputs may further be comprised of a biological extraction 320, wherein biological extraction 320 is described in detail above, with reference to FIG. 1. Biological extraction 320 may include any biomarker, chemical, lipid, protein, carbohydrate, specimen, or the like thereof. For example, and without limitation, a biological extraction may indicate an increase of blood flow to an area due to a rash.

Figure 4:
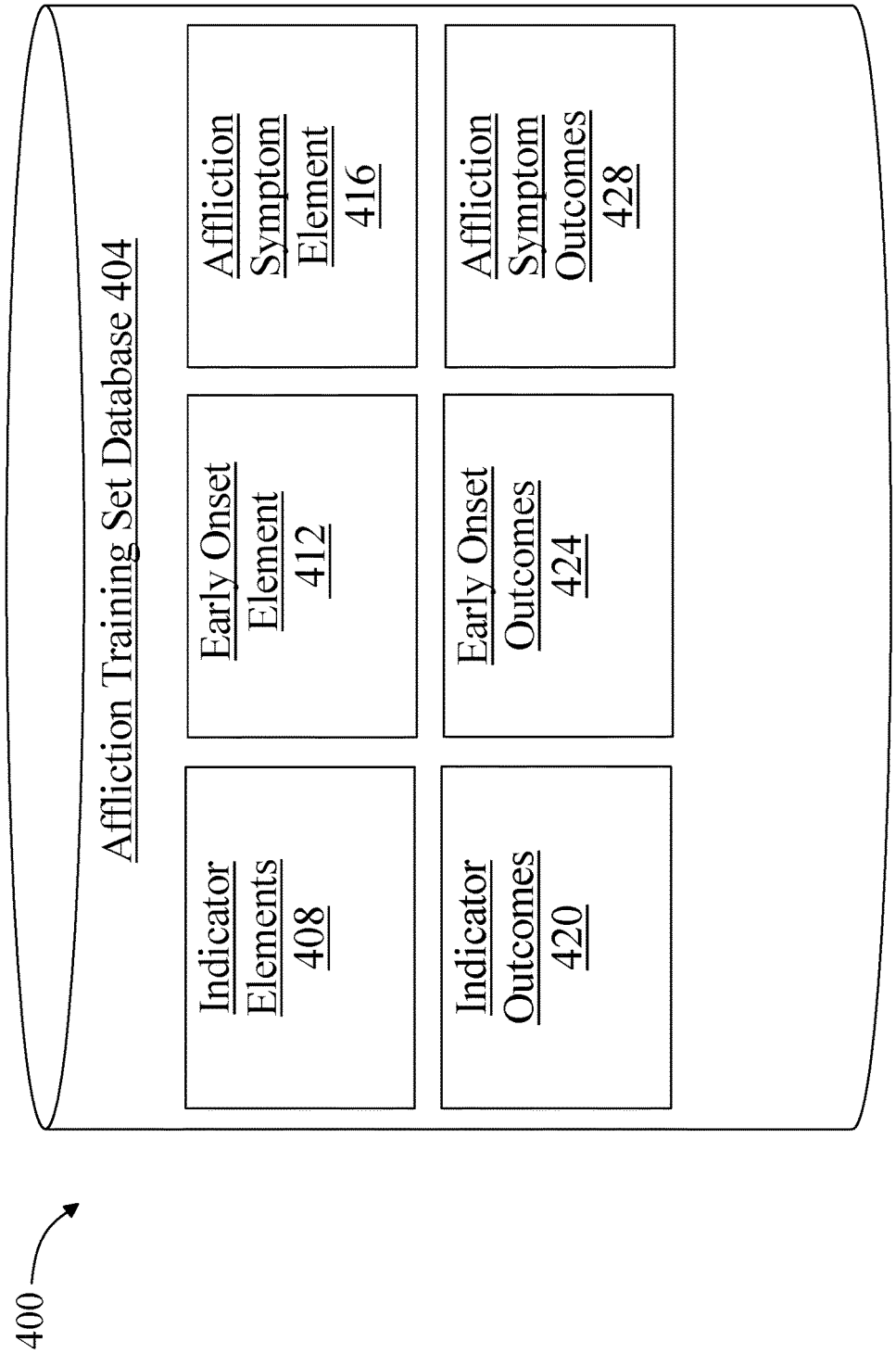
FIG. 4 is a block diagram of an exemplary embodiment of an affliction training set database according to an embodiment of the invention.

Now referring to FIG. 4, an exemplary embodiment 400 of an affliction training set database 404 is illustrated. Database may be implemented, without limitation, as a relational database, a key-value retrieval database such as a NOSQL database, or any other format or structure for use as a database that a person skilled in the art would recognize as suitable upon review of the entirety of this disclosure. Database may alternatively or additionally be implemented using a distributed data storage protocol and/or data structure, such as a distributed hash table or the like. Database may include a plurality of data entries and/or records as described above. Data entries in a database may be flagged with or linked to one or more additional elements of information, which may be reflected in data entry cells and/or in linked tables such as tables related by one or more indices in a relational database. Persons skilled in the art, upon reviewing the entirety of this disclosure, will be aware of various ways in which data entries in a database may store, retrieve, organize, and/or reflect data and/or records as used herein, as well as categories and/or populations of data consistently with this disclosure. Affliction training set database 404 may include an indicator element 408, which may indicate the proneness of developing an affliction. This may include, without limitation, markers such as proteins, cells, vitamins, electrolytes, or chemicals present in a user that indicate a predisposition for developing an affliction in the future. For example, and without limitation, an indicator element may be a high concentration of glucose in the blood, which may be an indicator of diabetes. Affliction training set database 404 may include an early onset element 412, which may indicate the start, beginning, or birth of a user affliction. For example, early onset marker set 412 may include, but is not limited to, HLA-DRB1, Anti-CCP antibodies, or HLA-DR4 for the early onset identification of rheumatoid arthritis. Affliction training set database 404 may include an affliction symptom element 416, which may indicate an active affliction that is presenting symptoms in a user. For instance, affliction symptom element 416 may include, without limitation, markers such as interleukin-6, tumor necrosis factor receptor type I, vascular cell adhesion molecule 1, epidermal growth factor, vascular endothelial growth factor A, YKL-40, matrix metalloproteinase 1, matrix metalloproteinase 3, C-reactive protein, serum amyloid A, Leptin, or resistin for rheumatoid arthritis. Affliction training set database 404 may include an indicator outcome 420, which may indicate the outcome of an ensuing affliction. In an embodiment, and without limitation, an indicator outcome may be the development of an early onset markers such as those described and/or cholesterol, NGAL, KIM-1, Cystatin-C, and the like thereof. Affliction training set database 404 may include an early onset outcome 424, which may include affliction results associated with an early onset status of an affliction. In an embodiment, early onset outcome, 424 may include an affliction symptom outcome. In an embodiment, early onset outcome 424 may include affliction results associated with early stages of an affliction. Early stages of an affliction may include minor symptoms such as cough, fever, shortness of breath, and the like thereof. Affliction training set database 404 may include an affliction symptom outcome, which may include affliction results associated with the late stages of an affliction. In an embodiment, affliction symptom outcome 428 may include outcome associated with the late stage of an affliction result. For example, and without limitation, affliction results may include affliction symptoms such as comorbidities, death, cognitive dysfunction, chronic fatigue, paralysis, and the like thereof.

Figure 5:
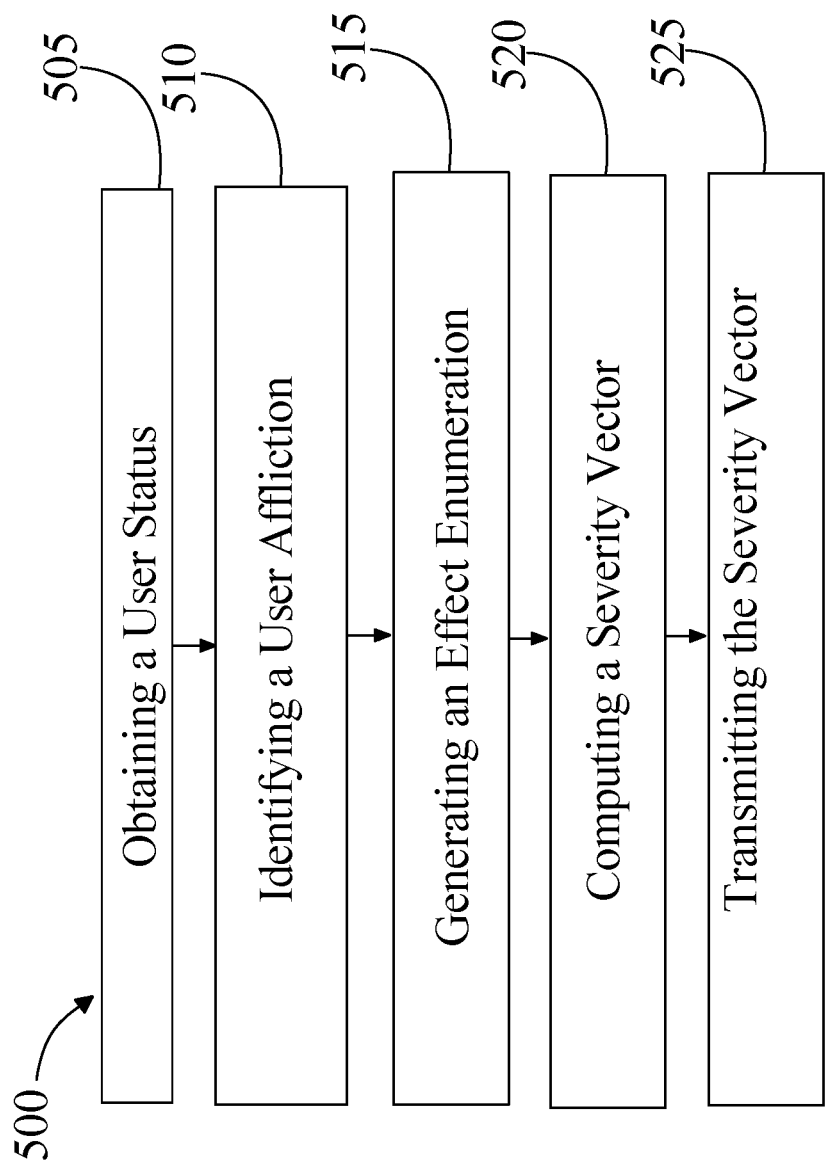
FIG. 5 is a process flow diagram illustrating an exemplary embodiment of a method of presenting a severity vector.

Now referring to FIG. 5, an exemplary embodiment of a method 500 of presenting a severity vector is illustrated. At step 505, a computing device 1-4 obtains a user status 112 from a remote device 108. User status 112 includes any of the user status 112 as described above in reference to FIGS. 1-4. For instance, and without limitation, a user status 112 may include of one or more affliction vectors relating to the user, wherein an affliction vector is further comprised of one or more qualitative elements that may indicate the current health status of a user. For example, an affliction vector may include, a family member entering an element relating to a user affliction vector. Remote device 108 includes any of the remote device 108 as described above in reference to FIGS. 1-4. For instance, and without limitation, remote device 112 may include a computing device, such as a mobile device, laptop, tablet, computer, desktop, and the like thereof.

With continued reference to FIG. 5, at step 510, computing device 104 identifies a user affliction 128 as a function of an affliction classifier 116. User affliction 128 includes any of the user affliction 128 as described above in FIGS. 1-4. For instance, and without limitation, user affliction 128 may consist of any list or collection of ailments relating to a physical, spiritual, and/or psychological element of a user. For example, and without limitation, a user affliction may include COVID-19, chakra blockage, and/or depression. Affliction classifier 116 includes any of the affliction classifier 116 as described above in FIGS. 1-4. For instance, and without limitation, affliction classifier may comprise qualitative elements, such as medical lineage, medical history, or physician examination and may output mensurable outputs. Mensurable outputs may include, without limitation, a decimal, binary, octal, hexadecimal, or duodecimal number system. Computing device 104 may identify affliction classifier 116 as a function of one or more machine-learning processes as described above in reference to FIGS. 1-4. Computing device 104 may identify affliction classifier using a user machine-learning process 120. User machine-learning process 120 includes any of the user machine-learning process 120 as described above in reference to FIGS. 1-5. For instance, and without limitation, user machine-learning process 120 may include a supervised machine-learning process or an unsupervised machine-learning process. User machine-learning process 120 may include a classification process, such as for example naïve Bayes, k-nearest neighbor, decision tree, and/or random forest. Classification processes include any of the classification processes as described above in reference to FIGS. 1-4. User machine-learning process 120 is configured using user training set 124. User training set 124 includes any of the user training set 124 as described above in reference to FIGS. 1-4. User training set 124 may include, without limitation, one or more user elements correlated to one or more afflictions, wherein a user element includes any qualitative and/or mensurable element relating to the user. For example, and without limitation, user training set 124 may correlate a high concentration of glucose in the user to diabetes.

With continued reference to FIG. 5, at step 515, computing device 104 generates an effect enumeration 132 as a function of the user affliction 128. Effect enumeration 132 includes any of the effect enumeration 132 as described above in reference to FIGS. 1-4. For instance, and without limitation, effect enumeration may consist of the probability of developing subsequent symptoms associated with user affliction 128. For example, and without limitation, effect enumeration may generate an effect enumeration of fever, coughing, headache, and shortness of breath for the affliction of influenza. Effect enumeration 132 may be generated as a function of one or more machine-learning processes as described above in reference to FIGS. 1-4. Computing device 104 may generate effect enumeration 132 using an affliction machine-learning process 140. Affliction machine-learning process 140 includes any of the affliction machine-learning process 140 as described above in reference to FIG. 1. For instance, and without limitation, affliction machine-learning process 140 may include a supervised machine-learning process or an unsupervised machine-learning process. Affliction machine-learning process 140 may include a classification process, such as for example naïve Bayes, k-nearest neighbor, decision tree, and/or random forest. Classification processes include any of the classification processes as described above in reference to FIGS. 1-4. Affliction machine-learning process 140 is configured using affliction training set 136. Affliction training set 136 includes any of the affliction training set 136 as described above in reference to FIGS. 1-4. Affliction training set 136 may include, without limitation, at least a first element of an afflictions state and at least a first affliction result. For example, a user may have signs, symptoms, and impacts of a shortness of breath, which correlates to the subsequent affliction result of coughing.

With continued reference to FIG. 5, at step 520, computing device 104 calculates a severity vector 144 as a function of the effect enumeration 132. Severity vector 144 includes any of the severity vector 144 as described above in reference to FIGS. 1-4. For example, and without limitation, severity vector 144 may indicate a proneness for developing respiratory distress as a function of influenza being a user affliction. Severity vector 144 may be comprised of a measurable index relating to the proneness of developing affliction symptoms. For example, and without limitation, a user affliction may be COVID-19 and may have a medical history of ischemic heart disease, warranting a value of 100 for a severity vector in the proneness of developing myocarditis as a result of COVID-19. Severity vector 144 may be calculated using a machine-learning process. Computing device 104 may calculate severity vector 144 using a severity machine-learning process 152. Severity machine-learning process 152 includes any of the severity machine-learning process 152 as described above in reference to FIGS. 1-4. For instance, and without limitation, severity machine-learning process 152 may include a supervised machine-learning process or an unsupervised machine-learning process. Severity machine-learning process 152 may include a classification process, such as for example naïve Bayes, k-nearest neighbor, decision tree, and/or random forest. Classification processes include any of the classification processes as described above in reference to FIGS. 1-4. Severity machine-learning process 152 is configured using severity training set 148. Severity training set 152 includes any of the severity training set 152 as described above in reference to FIGS. 1-4. Severity training set 152 may include, without limitation, effect enumeration 132 to an affliction status, wherein an affliction status relates to the current state of an affliction. For example, a user may have symptoms relating to COVID-19 and may be experiencing a cough and fever, wherein the affliction status is early and has not elevated to pneumonia, decreased $O_2$ saturation level, Guillain-Barre syndrome, myocarditis, ARDS, death, and the like thereof.

With continued reference to FIG. 5, at step 525, computing device 104 transmits severity vector 144 on remote device 108. Remote device 108 may include an additional computing device, such as a mobile device, laptop, desktop, computer, and the like. Remote device 108 may transmit and/or receive one or more inputs from computing device 104 utilizing any network methodology as described herein. For example, remote device 132 may display severity vector 144 of a plurality of severity vectors associated with one or more user afflictions. For example, a user may have a history of obesity, and may have contracted COVID-19, wherein obesity may weaken the heart, leading to a high severity vector of developing myocarditis as a function of the COVID-19 infection.

It is to be noted that any one or more of the aspects and embodiments described herein may be conveniently implemented using one or more machines (e.g., one or more computing devices that are utilized as a user computing device for an electronic document, one or more server devices, such as a document server, etc.) programmed according to the teachings of the present specification, as will be apparent to those of ordinary skill in the computer art. Appropriate software coding can readily be prepared by skilled programmers based on the teachings of the present disclosure, as will be apparent to those of ordinary skill in the software art. Aspects and implementations discussed above employing software and/or software modules may also include appropriate hardware for assisting in the implementation of the machine executable instructions of the software and/or software module.

Such software may be a computer program product that employs a machine-readable storage medium. A machine-readable storage medium may be any medium that is capable of storing and/or encoding a sequence of instructions for execution by a machine (e.g., a computing device) and that causes the machine to perform any one of the methodologies and/or embodiments described herein. Examples of a machine-readable storage medium include, but are not limited to, a magnetic disk, an optical disc (e.g., CD, CD-R, DVD, DVD-R, etc.), a magneto-optical disk, a read-only memory "ROM" device, a random access memory "RAM" device, a magnetic card, an optical card, a solid-state memory device, an EPROM, an EEPROM, and any combinations thereof. A machine-readable medium, as used herein, is intended to include a single medium as well as a collection of physically separate media, such as, for example, a collection of compact discs or one or more hard disk drives in combination with a computer memory. As used herein, a machine-readable storage medium does not include transitory forms of signal transmission.

Such software may also include information (e.g., data) carried as a data signal on a data carrier, such as a carrier wave. For example, machine-executable information may be included as a data-carrying signal embodied in a data carrier in which the signal encodes a sequence of instruction, or portion thereof, for execution by a machine (e.g., a computing device) and any related information (e.g., data structures and data) that causes the machine to perform any one of the methodologies and/or embodiments described herein.

Examples of a computing device include, but are not limited to, an electronic book reading device, a computer workstation, a terminal computer, a server computer, a handheld device (e.g., a tablet computer, a smartphone, etc.), a web appliance, a network router, a network switch, a network bridge, any machine capable of executing a sequence of instructions that specify an action to be taken by that machine, and any combinations thereof. In one example, a computing device may include and/or be included in a kiosk.

Figure 6:
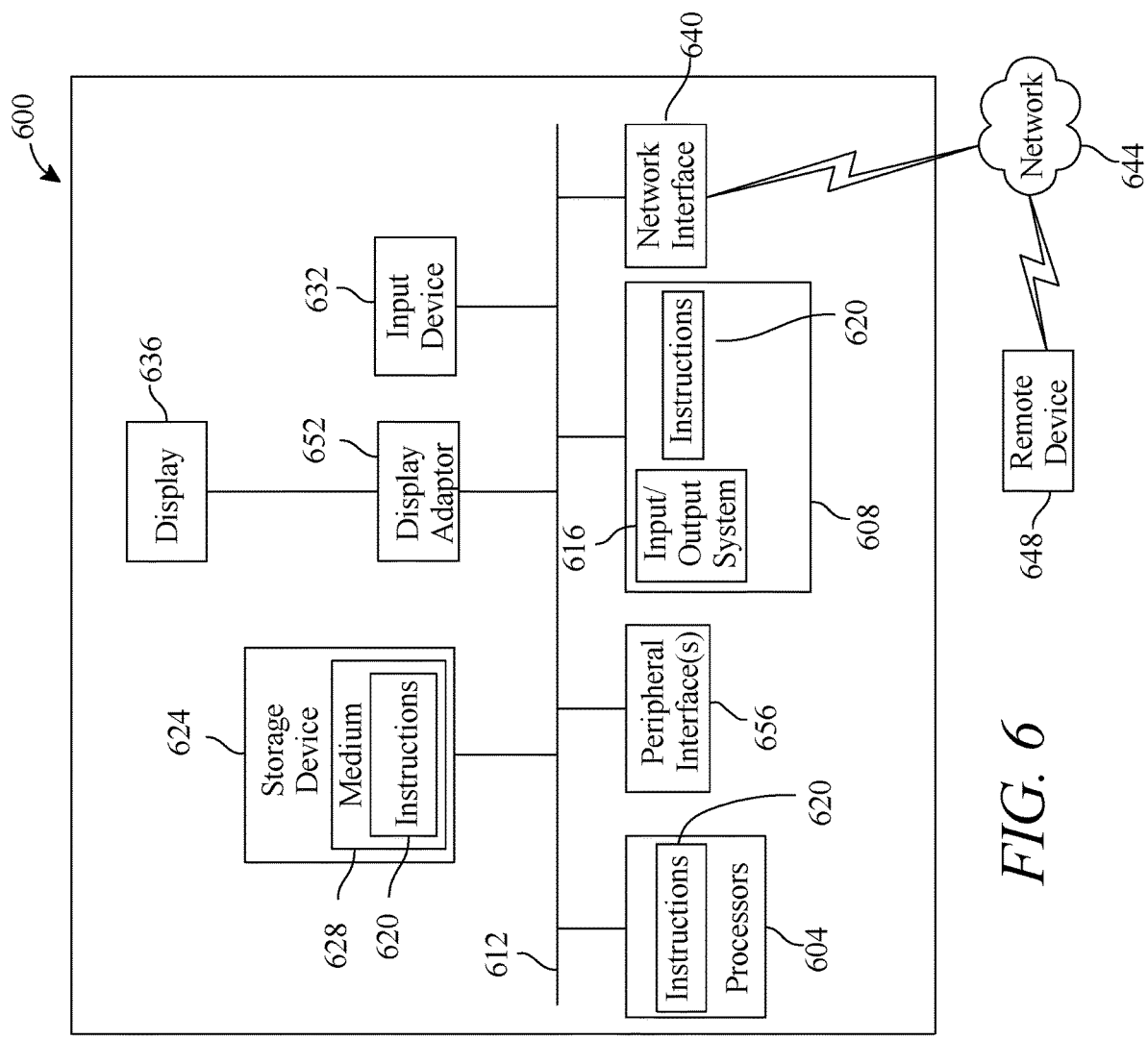
FIG. 6 is a block diagram of a computing system that can be used to implement any one or more of the methodologies disclosed herein and any one or more portions thereof.

FIG. 6 shows a diagrammatic representation of one embodiment of a computing device in the exemplary form of a computer system 600 within which a set of instructions for causing a control system to perform any one or more of the aspects and/or methodologies of the present disclosure may be executed. It is also contemplated that multiple computing devices may be utilized to implement a specially configured set of instructions for causing one or more of the devices to perform any one or more of the aspects and/or methodologies of the present disclosure. Computer system 600 includes a processor 604 and a memory 608 that communicate with each other, and with other components, via a bus 612. Bus 612 may include any of several types of bus structures including, but not limited to, a memory bus, a memory controller, a peripheral bus, a local bus, and any combinations thereof, using any of a variety of bus architectures.

Processor 604 may include any suitable processor, such as without limitation a processor incorporating logical circuitry for performing arithmetic and logical operations, such as an arithmetic and logic unit (ALU), which may be regulated with a state machine and directed by operational inputs from memory and/or sensors; processor 604 may be organized according to Von Neumann and/or Harvard architecture as a non-limiting example. Processor 604 may include, incorporate, and/or be incorporated in, without limitation, a micro-controller, microprocessor, digital signal processor (DSP), Field Programmable Gate Array (FPGA), Complex Programmable Logic Device (CPLD), Graphical Processing Unit (GPU), general purpose GPU, Tensor Processing Unit (TPU), analog or mixed signal processor, Trusted Platform Module (TPM), a floating point unit (FPU), and/or system on a chip (SoC)

Memory 608 may include various components (e.g., machine-readable media) including, but not limited to, a random-access memory component, a read only component, and any combinations thereof. In one example, a basic input/output system 616 (BIOS), including basic routines that help to transfer information between elements within computer system 600, such as during start-up, may be stored in memory 608. Memory 608 may also include (e.g., stored on one or more machine-readable media) instructions (e.g., software) 620 embodying any one or more of the aspects and/or methodologies of the present disclosure. In another example, memory 608 may further include any number of program modules including, but not limited to, an operating system, one or more application programs, other program modules, program data, and any combinations thereof.

Computer system 600 may also include a storage device 624. Examples of a storage device (e.g., storage device 624) include, but are not limited to, a hard disk drive, a magnetic disk drive, an optical disc drive in combination with an optical medium, a solid-state memory device, and any combinations thereof. Storage device 624 may be connected to bus 612 by an appropriate interface (not shown). Example interfaces include, but are not limited to, SCSI, advanced technology attachment (ATA), serial ATA, universal serial bus (USB), IEEE 1394 (FIREWIRE), and any combinations thereof. In one example, storage device 624 (or one or more components thereof) may be removably interfaced with computer system 600 (e.g., via an external port connector (not shown)). Particularly, storage device 624 and an associated machine-readable medium 628 may provide nonvolatile and/or volatile storage of machine-readable instructions, data structures, program modules, and/or other data for computer system 600. In one example, software 620 may reside, completely or partially, within machine-readable medium 628. In another example, software 620 may reside, completely or partially, within processor 604.

Computer system 600 may also include an input device 632. In one example, a user of computer system 600 may enter commands and/or other information into computer system 600 via input device 632. Examples of an input device 632 include, but are not limited to, an alpha-numeric input device (e.g., a keyboard), a pointing device, a joystick, a gamepad, an audio input device (e.g., a microphone, a voice response system, etc.), a cursor control device (e.g., a mouse), a touchpad, an optical scanner, a video capture device (e.g., a still camera, a video camera), a touchscreen, and any combinations thereof. Input device 632 may be interfaced to bus 612 via any of a variety of interfaces (not shown) including, but not limited to, a serial interface, a parallel interface, a game port, a USB interface, a FIREWIRE interface, a direct interface to bus 612, and any combinations thereof. Input device 632 may include a touch screen interface that may be a part of or separate from display 636, discussed further below. Input device 632 may be utilized as a user selection device for selecting one or more graphical representations in a graphical interface as described above.

A user may also input commands and/or other information to computer system 600 via storage device 624 (e.g., a removable disk drive, a flash drive, etc.) and/or network interface device 640. A network interface device, such as network interface device 640, may be utilized for connecting computer system 600 to one or more of a variety of networks, such as network 644, and one or more remote devices 648 connected thereto. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network, such as network 644, may employ a wired and/or a wireless mode of communication. In general, any network topology may be used. Information (e.g., data, software 620, etc.) may be communicated to and/or from computer system 600 via network interface device 640.

Computer system 600 may further include a video display adapter 652 for communicating a displayable image to a display device, such as display device 636. Examples of a display device include, but are not limited to, a liquid crystal display (LCD), a cathode ray tube (CRT), a plasma display, a light emitting diode (LED) display, and any combinations thereof. Display adapter 652 and display device 636 may be utilized in combination with processor 604 to provide graphical representations of aspects of the present disclosure. In addition to a display device, computer system 600 may include one or more other peripheral output devices including, but not limited to, an audio speaker, a printer, and any combinations thereof. Such peripheral output devices may be connected to bus 612 via a peripheral interface 656. Examples of a peripheral interface include, but are not limited to, a serial port, a USB connection, a FIREWIRE connection, a parallel connection, and any combinations thereof.

The foregoing has been a detailed description of illustrative embodiments of the invention. Various modifications and additions can be made without departing from the spirit and scope of this invention. Features of each of the various embodiments described above may be combined with features of other described embodiments as appropriate in order to provide a multiplicity of feature combinations in associated new embodiments. Furthermore, while the foregoing describes a number of separate embodiments, what has been described herein is merely illustrative of the application of the principles of the present invention. Additionally, although particular methods herein may be illustrated and/or described as being performed in a specific order, the ordering is highly variable within ordinary skill to achieve systems and methods according to the present disclosure. Accordingly, this description is meant to be taken only by way of example, and not to otherwise limit the scope of this invention.

Exemplary embodiments have been disclosed above and illustrated in the accompanying drawings. It will be understood by those skilled in the art that various changes, omissions, and additions may be made to that which is specifically disclosed herein without departing from the spirit and scope of the present invention.

What is claimed is:

1. A system for transmitting a severity vector, the system comprising:
a computing device, the computing device configured to:
obtain, from a remote device, a user status and a biological extraction from a user;
identify a user affliction from a predetermined list of user afflictions as a function of the user status and an affliction classifier which includes clustering of data associated with both physical and psychological afflictions, wherein data associated with a first physical affliction and a related first psychological affliction is clustered in a single category, wherein the user affliction includes an identified physical affliction and an identified psychological affliction related to the identified physical affliction as determined by the clustering of data included in the affliction classifier;
generate an effect enumeration machine-learning process, wherein generating the effect enumeration machine-learning process further comprises:
obtaining an affliction training set, wherein the affliction training set relates at least a first vector of an affliction state and at least a first affliction result;
training the effect enumeration machine-learning process as a function of the affliction training set and a first supervised machine-learning algorithm; and
generate, using the effect enumeration machine-learning process, an effect enumeration, wherein the effect enumeration machine-learning process inputs the user affliction and outputs the effect enumeration, wherein the effect enumeration includes a plurality of enumeration vectors associated with the affliction, wherein each enumeration vector comprises at least an affliction symptom outcome;
compute a severity vector as a function of the effect enumeration and the biological extraction from the user, wherein the severity vector comprises:
a user affliction progression probability; and
at least an affliction complication, wherein the at least an affliction complication correlates the biological extraction from the user to a symptom of the user affliction; and
wherein the computing of the severity vector comprises:
obtaining a severity training set that relates an effect enumeration to an affliction status;
training a severity machine-learning process as a function of the severity training set and a second supervised machine-learning algorithm, wherein the second supervised machine-learning algorithm comprises a scoring function, wherein a relationship is detected between the severity training set and the severity vector as a function of the scoring function, wherein the scoring function maximizes the probability that a given severity training set is associated with a given severity vector to minimize the probability that a given severity training set is not associated with a given severity vector; and
computing the severity vector as a function of the biological extraction from the user and the trained severity machine-learning process; and
transmit the severity vector to the remote device.

2. The system of claim 1, wherein the user status comprises at least an affliction vector.

3. The system of claim 1, wherein the affliction classifier comprises a machine-learning model generated by a classification algorithm.

4. The system of claim 3, wherein the affliction classifier is configured to obtain vectors that relate to qualities of a user.

5. The system of claim 3, wherein the affliction classifier is configured to generate mensurable outputs.

6. The system of claim 3, wherein the computing device is configured to identify the user affliction by:
obtaining a user training set relating at least a user vector to an affliction; and
identifying the affliction classifier as a function of the user training set using a user machine-learning process, the user machine-learning process configured using the user training set.

7. The system of claim 1, wherein the severity vector is comprised of measurable index relating to the proneness of developing affliction traits.

8. A method for transmitting a severity vector, the method comprising:
obtaining, by a computing device, from a remote device, a user status and a biological extraction from a user;
identifying, by the computing device, a user affliction from a predetermined list of user afflictions as a function of the user status and an affliction classifier which includes clustering of data associated with both physical and psychological afflictions, wherein data associated with a first physical affliction and a related first psychological affliction is clustered in a single category, wherein the user affliction includes an identified physical affliction and an identified psychological affliction related to the identified physical affliction as determined by the clustering of data included in the affliction classifier;
generating, by the computing device, an effect enumeration machine-learning process, wherein generating the effect enumeration machine-learning process further comprises:
obtaining an affliction training set, wherein the affliction training set relates at least a first vector of an affliction state and at least a first affliction result;
training the effect enumeration machine-learning module as a function of the affliction training set and a first supervised machine-learning algorithm; and
generating, by the effect enumeration machine-learning process, an effect enumeration, wherein the effect enumeration machine-learning process inputs the user affliction and outputs the effect enumeration, wherein the effect enumeration includes a plurality of enumeration vectors associated with the affliction, wherein each enumeration vector comprises at least an affliction symptom outcome;
computing, by the computing device, a severity vector as a function of the effect enumeration and the biological extraction from the user, wherein the severity vector comprises:
a user affliction progression probability; and
at least an affliction complication, wherein the at least an affliction complication correlates the biological extraction from the user to a symptom of the user affliction; and
wherein the computing of the severity vector comprises:
obtaining a severity training set that relates an effect enumeration to an affliction status;
training a severity machine-learning process as a function of the severity training set and a second supervised machine-learning algorithm, wherein the second supervised machine-learning algorithm comprises a scoring function, wherein a relationship is detected between the severity training set and the severity vector as a function of the scoring function, wherein the scoring function maximizes the probability that a given severity training set is associated with a given severity vector to minimize the probability that a given severity training set is not associated with a given severity vector;
computing the severity vector as a function of the biological extraction from the user and the trained severity machine-learning process; and
transmitting, by the computing device, the severity vector to the remote device.

9. The method of claim 8, wherein the user status comprises at least an affliction vector.

10. The method of claim 8, wherein the affliction classifier comprises a machine-learning model generated by a classification algorithm.

11. The method of claim 10, wherein the affliction classifier is comprised of vectors that relate to qualities of a user.

12. The method of claim 10, wherein the affliction classifier is configured to generate mensurable outputs.

13. The method of claim 10, identifying the user affliction further comprises:
obtaining a user training set relating at least a user vector to an affliction; and
identifying the affliction classifier as a function of the user training set using a user machine-learning process, the user machine-learning process configured using the user training set.

14. The method of claim 8, wherein the severity vector is comprised of a measurable index relating to the proneness of developing affliction traits.

15. The system of claim 1, wherein the affliction classifier includes a qualitative element, wherein the qualitative element comprises of medical lineage.

16. The method of claim 8, wherein the affliction classifier includes a qualitative element, wherein the qualitative element comprises of medical lineage.

17. The system of claim 1, wherein transmitting the severity vector to the remote device includes displaying the severity vector on the remote device along with a plurality of severity vectors associated with one or more user afflictions, wherein displaying the severity vector includes allowing the user to navigate through the plurality of severity vectors to determine the affliction progression probability.

18. The method of claim 8, wherein transmitting the severity vector to the remote device includes displaying the severity vector on the remote device along with a plurality of severity vectors associated with one or more user afflictions, wherein displaying the severity vector includes allowing the user to navigate through the plurality of severity vectors to determine the affliction progression probability.

19. The system of claim 1, obtaining the user status comprises receiving a physician input.

20. The method of claim 8, obtaining the user status comprises receiving a physician input.

* * * * *